United States Patent
Kim et al.

(10) Patent No.: US 10,648,733 B2
(45) Date of Patent: *May 12, 2020

(54) WASHSTAND FURNITURE

(71) Applicant: LG ELECTRONICS INC., Seoul (KR)

(72) Inventors: Jongseok Kim, Seoul (KR); Daeyun Park, Seoul (KR); Inhyung Yang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 114 days.

This patent is subject to a terminal disclaimer.

(21) Appl. No.: 15/915,480

(22) Filed: Mar. 8, 2018

(65) Prior Publication Data

US 2018/0259261 A1    Sep. 13, 2018

(30) Foreign Application Priority Data

Mar. 8, 2017 (KR) .................. 10-2017-0029738

(51) Int. Cl.
| | |
|---|---|
| *F26B 9/06* | (2006.01) |
| *E03C 1/14* | (2006.01) |
| *A47K 1/00* | (2006.01) |
| *A61L 2/10* | (2006.01) |
| *F26B 3/04* | (2006.01) |
| *E03C 1/04* | (2006.01) |
| *E03C 1/32* | (2006.01) |
| *E03C 1/23* | (2006.01) |

(52) U.S. Cl.
CPC .............. *F26B 9/066* (2013.01); *A47K 1/00* (2013.01); *A61L 2/10* (2013.01); *E03C 1/14* (2013.01); *F26B 3/04* (2013.01); *A61L 2202/17* (2013.01); *E03C 1/04* (2013.01); *E03C 1/23* (2013.01); *E03C 1/32* (2013.01); *E03C 2201/40* (2013.01)

(58) Field of Classification Search
CPC .... A47K 1/00; A47K 1/02; E03C 1/32; F26B 3/04; F26B 9/066; F26B 21/00; F26B 21/003; F26B 25/06; F26B 25/066; F26B 25/14; F26B 25/18; H02J 50/10
USPC ........................................................... 4/630
See application file for complete search history.

(56) References Cited

U.S. PATENT DOCUMENTS

| | | | |
|---|---|---|---|
| 2,175,329 A | * | 10/1939 | Watt .................. E03C 1/044 4/630 |
| 2,287,657 A | | 6/1942 | Wisckol |
| 4,146,405 A | | 3/1979 | Timmer et al. |
| 5,522,411 A | | 6/1996 | Johnson |

(Continued)

OTHER PUBLICATIONS

U.S. Office Action dated May 31, 2019 issued in U.S. Appl. No. 15/915,193.

(Continued)

*Primary Examiner* — Janie M Loeppke
(74) *Attorney, Agent, or Firm* — Ked & Associates, LLP

(57) ABSTRACT

Washstand furniture includes: a wash device including a wash bowl, a water supply assembly for supplying water to the wash bowl, and a drainage assembly for draining the water supplied to the wash bowl; a cabinet provided under the wash bowl, the cabinet having a space defined therein; and a residual-water-suction-device-drying module provided inside the cabinet for receiving and drying separate components of a residual water suction device for suctioning liquid.

20 Claims, 11 Drawing Sheets

(56) References Cited

U.S. PATENT DOCUMENTS

| | | | |
|---|---|---|---|
| 5,702,115 | A | 12/1997 | Pool |
| 5,727,579 | A | 3/1998 | Chardack |
| 5,934,298 | A | 8/1999 | Singh |
| 6,802,578 | B1 | 10/2004 | Lang et al. |
| 8,245,414 | B2 | 8/2012 | Watson et al. |
| 8,283,812 | B2 * | 10/2012 | Azancot ............... H01F 38/14 307/328 |
| 8,991,067 | B2 * | 3/2015 | Zielinski ............... F26B 5/044 34/403 |
| 9,255,733 | B2 * | 2/2016 | Bagwell ............... F26B 3/04 |
| 9,887,562 | B2 | 2/2018 | Racenet et al. |
| 10,317,137 | B2 | 6/2019 | Kim et al. |
| 2007/0151302 | A1 | 7/2007 | Kendall et al. |
| 2007/0157378 | A1 | 7/2007 | Kendall et al. |
| 2008/0256826 | A1 * | 10/2008 | Zarembinski ........ D06F 58/10 34/562 |
| 2014/0366262 | A1 | 12/2014 | Flynn |
| 2015/0252515 | A1 | 9/2015 | Henry et al. |
| 2016/0128528 | A1 | 5/2016 | Stewen et al. |

OTHER PUBLICATIONS

U.S. Office Action dated Oct. 5, 2018 issued in U.S. Appl. No. 15/915,216.
U.S. Notice of Allowance dated Oct. 19, 2018 issued in copending U.S. Appl. No. 15/915,236.
U.S. Office Action dated Oct. 2, 2019 issued in U.S. Appl. No. 15/915,401.
United States Office Action dated Sep. 13, 2019 issued in U.S. Appl. No. 15/915,332.
U.S. Appl. No. 15/915,193, filed Mar. 8, 2018.
U.S. Appl. No. 15/915,364, filed Mar. 8, 2018.
U.S. Appl. No. 15/915,267, filed Mar. 8, 2018.
U.S. Appl. No. 15/915,332, filed Mar. 8, 2018.
U.S. Appl. No. 15/915,401, filed Mar. 8, 2018.
U.S. Appl. No. 15/915,421, filed Mar. 8, 2018.

* cited by examiner (a)  (b)

(a)

(b)

WASHSTAND FURNITURE

CROSS-REFERENCE TO RELATED APPLICATIONS

This application claims priority under 35 U.S.C. § 119 to Korean Application No. 10-2017-0029738, filed on Mar. 8, 2017, whose entire disclosure is hereby incorporated by reference.

U.S. application Ser. Nos. 15/915,193; 15/915,364; 15/915,267; 15/915,332; 15/915,401; 15/915,480; 15/915,421; 15/915,216; 15/915,236, all filed on Mar. 8, 2018, are related and are hereby incorporated by reference in their entirety. Further, one of ordinary skill in the art will recognize that features disclosed in these above-noted applications may be combined in any combination with features disclosed herein.

BACKGROUND

1. Field

The present disclosure relates to washstand furniture that utilizes the space under a washstand, and more particularly to washstand furniture having a module received therein.

2. Background

Moisture may remain on the wall and/or the floor of a bathroom after the bathroom is used. If moisture on the wall or the floor of the bathroom is not removed properly, scaling may be formed, and this scaling may necessitate additional cleaning of the bathroom.

U.S. Patent Publication No. 2016/0128528 discloses a portable hard surface cleaning device (or a residual water suction device), which includes a water and air separation module, a suction port, and a drainage water tank. The device may function to remove moisture. For example, the residual water suction device may be used to suction moisture remaining in a bathroom, such as to remove moisture from a wall or floor of the bathroom. When the residual water suction device is used, moisture may be present within the residual water suction device. As a result, scaling may be formed inside the residual water suction device, or mildew may propagate within the residual water suction device. Consequently, a device that is not, itself, clean may be used to attempt to dry and clean the bathroom. For example, mildew in the device may be undesirably transferred to a surface of a bathroom during use to suction water from the surface.

The above reference is incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements, and wherein.

DETAILED DESCRIPTION

Exemplary embodiments of washstand furniture according to the present disclosure will be described with reference to the accompanying drawings.

Figure 1:
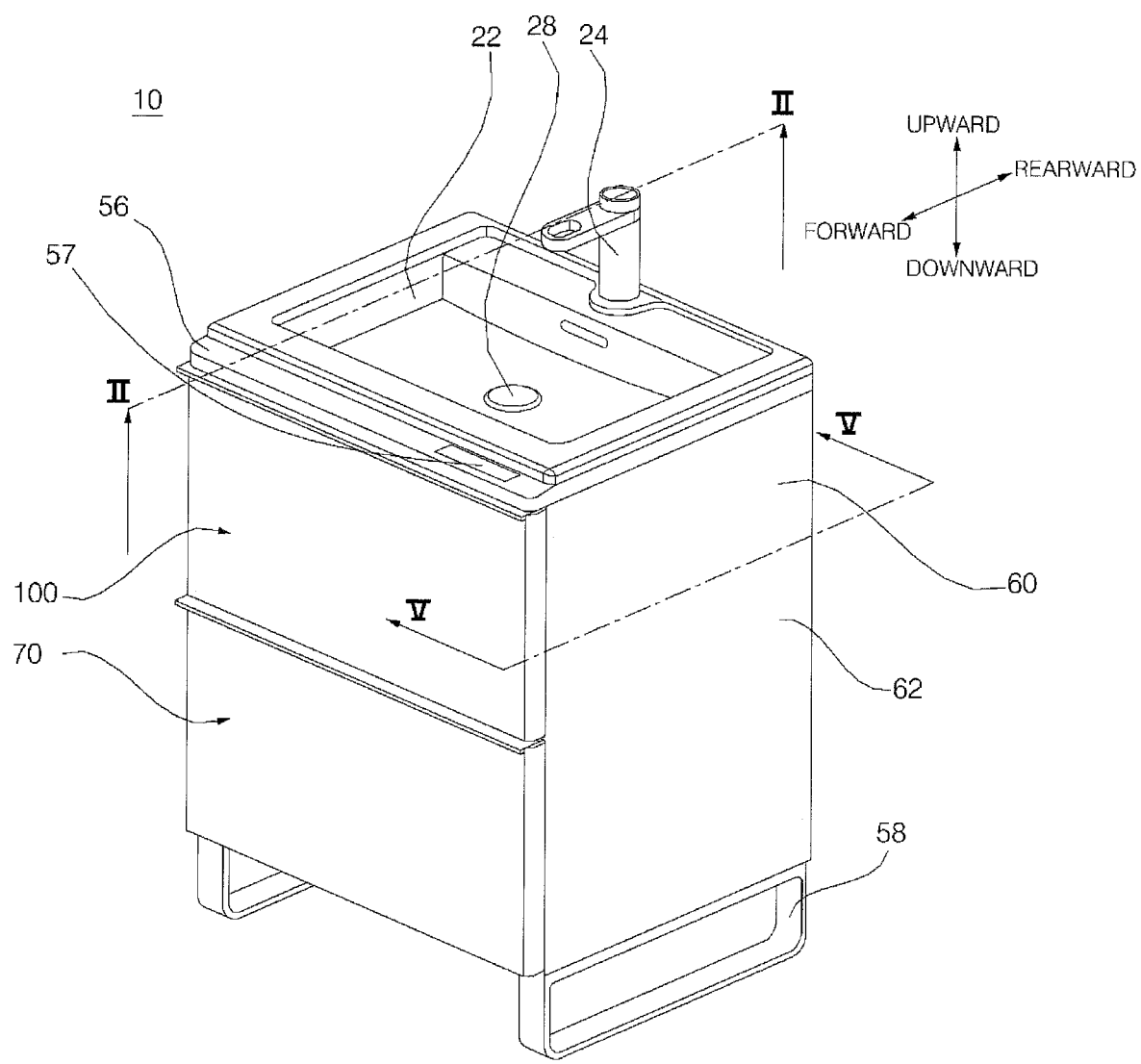
FIG. 1 is a perspective view showing washstand furniture according to an embodiment of the present disclosure.
Figure 2:
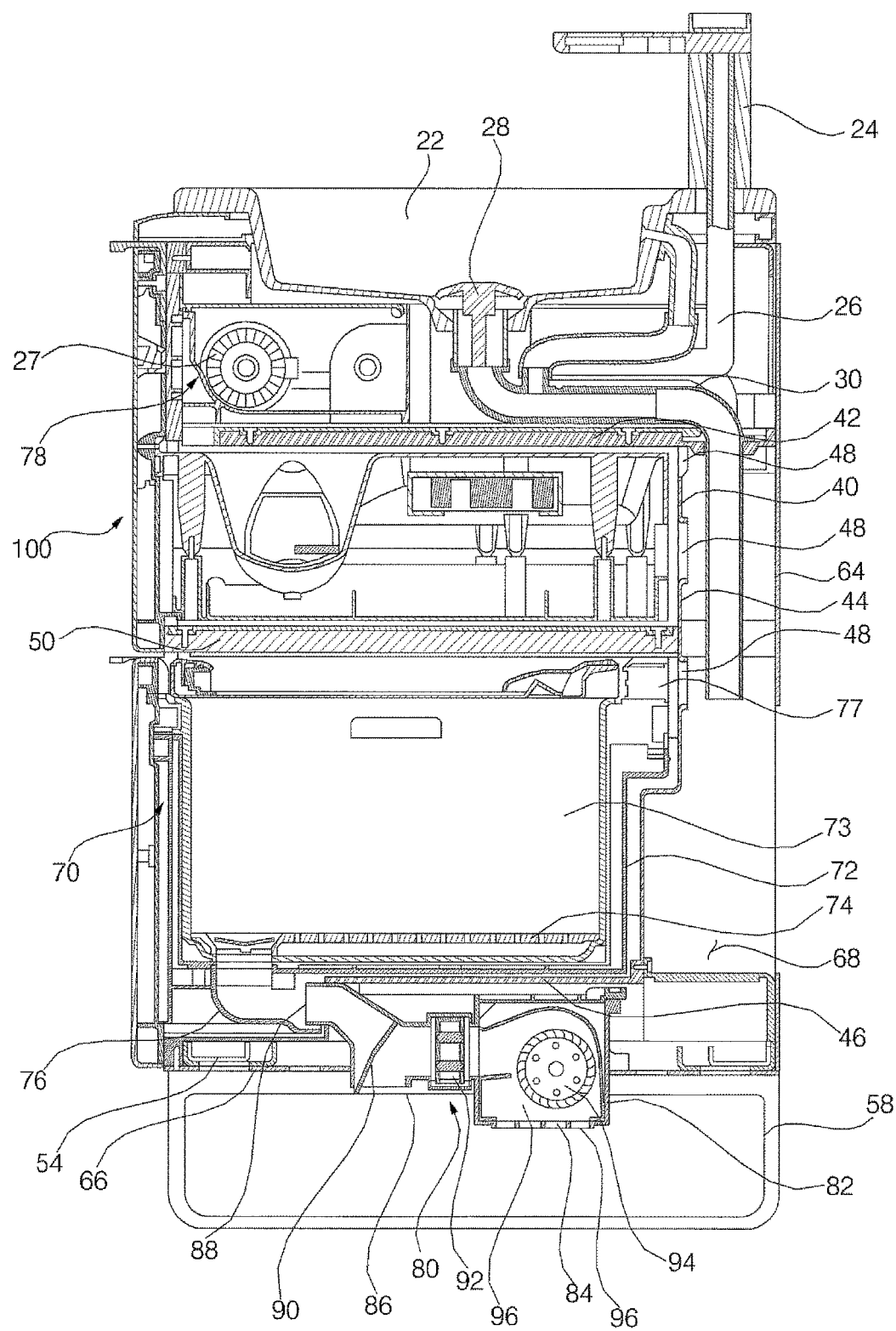
FIG. 2 is a sectional view taken along line II-II' of FIG. 1.

FIG. 1 is a perspective view showing washstand furniture according to an embodiment of the present disclosure, and FIG. 2 is a sectional view taken along line II-II' of FIG. 1. Hereinafter, the structure of washstand furniture (also referred to as a washstand or vanity) 10 according to this embodiment will be described with reference to FIGS. 1 and 2.

The washstand furniture 10 according to this embodiment may include: a wash device including a wash bowl (also referred to as a sink or basin), a water supply assembly (also referred to as a faucet or tap) that supplies water to the wash bowl, and a drainage assembly (or drain) that drains the water supplied to the wash bowl; an inner cabinet 40 that is provided under the wash bowl and may have a space defined therein; an outer cabinet 60 that covers the exterior of the inner cabinet; and a residual-water-suction-device-drying module (or -suction-device dryer) 100 that may be provided inside the inner cabinet, the residual-water-suction-device-drying module may include a plurality of receiving units (or cavities) to receive and dry separate components of a residual water suction device (or suction device) 200 (see FIG. 4) for suctioning liquid, wherein an external connection channel 68 that communicates with an outside of the washstand furniture may be defined between the inner cabinet and the outer cabinet, and the residual-water-suction-device-drying module may include a fan that generates an air flow from the external connection channel 68 and to the receiving units of the residual-water-suction-device-drying module 100.

Referring to FIG. 1, in the washstand furniture 10 according to one embodiment, a direction in which a module is withdrawn from the cabinet (e.g., away from a wall on which the washstand furniture 10 is mounted) may be referred to as a forward direction, a direction opposite the forward direction (e.g., toward a wall on which the washstand furniture 10 is mounted) may be referred to as a rearward direction, a direction in which the wash bowl is provided will be referred to as an upward direction, and a direction in which legs of the washstand furniture are provided may be referred to as a downward direction, but these orientations are provided for convenience of the flowing description and are not intended to limit the scope of the disclosure. For example, the module may be withdrawn from a side surface of the washstand furniture 10, and the washbowl is may be positioned at a side or below the cabinet.

The wash device is a device provided adjacent to the wall of a restroom, i.e. a washroom, and that allows a user to wash his/her face or hands. The wash device may include a wash bowl 22 that stores water used to perform washing, a water supply assembly to supply water to the wash bowl 22, and a drainage assembly that drains the supplied water from the wash bowl 22.

An enamel wash bowl or a ceramic wash bowl may be used as the wash bowl 22. In this embodiment, an enamel wash bowl may be used since the enamel wash bowl can be variably formed in various shapes, and the lower part of the enamel wash bowl can be easily coupled to the cabinet. The wash bowl 22 may be provided at am upper part or opening of the washstand furniture 10. In another example, the wash bowl 22 may be provided at a middle or lower portion of the washstand furniture 10.

The water supply assembly may include a water supply valve 24 that controls a supply of water to the wash bowl 22 and a water supply hose 26 that supplies water to the water supply valve 24. The water supply valve 24 may be provided at one side of the wash bowl 22 to supply water to that side of the wash bowl 22. The water supply hose 26 may include a hot water supply hose that supplies hot (e.g. heated) water and a separate cold water supply hose that supplies cold (e.g., unheated, room temperature) water. The water supply hose 26 may be connected to the outside of the washstand furniture 10 through the upper surface 42 of an inner cabinet 40, which will be described below.

The water supply assembly may further include a water purification filter 27 that filters or otherwise purifies the water that is introduced into the water supply hose 26. The water purification filter 27 may purify the water that is discharged to the wash bowl 22 via the water supply valve 24.

The drainage assembly may include a drainage pipe 30 that discharges the water from in the wash bowl 22 to an outside of the washstand furniture 10 and a popup valve 28 that selectively may prevent a flow of water through the drainage pipe. For example, the popup valve 28 may be closed to cause water to remain in the wash bowl 22 or may open to allow the water stored in the wash bowl 22 to move into the drainage pipe 30.

The cabinet, which defines the external appearance of the washstand furniture 10, may be provided under the wash device. The cabinet maintains the rigidity of the washstand furniture 10 and may have a space in which the module is received. In this embodiment, the interior of the cabinet may be hollow, and the front of the cabinet may be open to receive the module.

In this embodiment, the cabinet may include an inner cabinet 40 to receive the module therein and an outer cabinet 60 provided outside the inner cabinet 40 and to maintain a rigidity of the washstand furniture. In this embodiment, the washstand furniture 10 includes the inner cabinet 40 and the outer cabinet 60 that each provides a separate barrier to prevent water from being introduced into a module positioned in the inner cabinet 40.

In this embodiment, the inner cabinet 40 may be formed in the shape of a box, the interior of which is hollow and the front of which is open. In this embodiment, the outer cabinet 60 may be provided outside the inner cabinet 40. In this embodiment, the outer cabinet 60 may include side-outer cabinet walls 62 provided at opposite side surfaces of the inner cabinet 40, a rear-outer cabinet wall 64 provided at the rear surface 44 of the inner cabinet 40, and a base-outer cabinet wall 66 provided at the lower surface 46 of the inner cabinet 40.

The inner cabinet 40 may include, at the inside thereof, a rail member (not shown) to move the module into the inside or to the outside of the inner cabinet 40. The inner cabinet 40 may include, at a part thereof corresponding to a suction port or a discharge port of the module, a communication hole 48. The inner cabinet 40 may include a lower surface 46 thereof having a communication hole 48, which is connected to a discharge port of an air conditioner (or dryer) 80. A portion of a housing 82 may be formed around the discharge port of the air conditioner 80 that extends through the communication hole 48. The air conditioner 80 may be provided between the lower surface of the inner cabinet 40 and a base outer cabinet 68.

An external connection channel 68, through which air flows between the module and the outside of the washstand furniture 10, may be defined between the rear surface 44 of the inner cabinet 40 and the rear outer cabinet 64. The lower part of the external connection channel 68 may be open so as to be connected to the outside of the washstand furniture 10.

In one embodiment, in order to minimize the magnitude of the load of the wash device that is transmitted to the cabinet, the washstand furniture 10 may further include a frame 54 provided between the inner cabinet 40 and the outer cabinet 60.

The module 70, 100 may be received in the inner cabinet 40. In this embodiment, the module may be an electrically operated device received in the cabinet. A plurality of modules may be received in the cabinet.

In one embodiment, the washstand furniture 10 includes a first module (or heated drawer assembly) 70 and a second module (or drying drawer assembly) 100. The first module 70 may be provided at the lower part of the inner cabinet 40, and the second module 100 may be provided at the upper part of the inner cabinet 40 (e.g., above the first module 70).

In one embodiment, the washstand furniture 10 may further include a third module 78 provided between the inner cabinet 40 and the wash bowl 22. In this embodiment, the third module 78 may include a water purification filter 27 that purifies water that is supplied to the water supply assembly or a printed circuit board (not shown) to control electric power supplied to an air conditioner 80 or to the modules 70, 100 or to control the operation thereof.

The washstand furniture 10 may include a partition 50 that partitions an interior of the inner cabinet 40 into spaces for receiving a plurality of modules. The partition 50 may partition the interior of the inner cabinet 40 into separate spaces that receive the modules. For example, the second module 100 may be provided in the inner cabinet 40 above the partition 50, and the first module 70 may be provided in the inner cabinet 40 under the partition 50. In addition, a wire that supplies electric power to the module 70, 100 that is configured to move forward (e.g., outward) from the interior of the cabinet may be provided at the partition 50.

In the embodiment show in FIGS. 1 and 2, the washstand furniture 10 may also include an upper cover 56 provided between the wash bowl 22 and the cabinet, and the upper cover 56 may function primarily to block water falling from the wash bowl 22. The upper cover 56 may interconnect the wash bowl 22 and the cabinet. In this embodiment, the washstand furniture 10 may include an input unit (or user interface) 57 that allows a user to input a command to operate the air conditioner 80 or the other modules. In one example, the input unit 57 may be positioned at one side of the upper cover 56.

In this embodiment, the washstand furniture 10 may further include legs (or supports) 58 to space the cabinet apart from the floor of the bathroom by a predetermined distance.

In this configuration, the air conditioner 80 may discharge air to dehumidify the floor of the bathroom or to dry the interiors of the modules provided in the cabinet. The air conditioner 80 may discharges air through a first discharge port 86 facing the floor of the bathroom or through a second discharge port 88 connected to the interior of the cabinet using a fan 94.

In this embodiment, the air conditioner 80 may be provided under the inner cabinet 40. The air conditioner 80 may discharge air to the first module 70, which is provided in the inner cabinet 40, from under the inner cabinet 40. The air conditioner 80 may be positioned under the lower surface of the inner cabinet 40. The air conditioner 80 may be positioned so as to be spaced apart from the floor of the bathroom by at least a predetermined distance. The air conditioner 80 may be spaced apart from the floor of the bathroom by the predetermined distance to discharge air toward the floor of the bathroom. The air conditioner 80 may be positioned between the lower surface of the inner cabinet 40 and the base-outer cabinet wall 66. A portion of a housing 82 of the air conditioner 80 may protrude toward a lower side of the base-outer cabinet wall 66. The air conditioner 80 may be mounted to the base-outer cabinet wall 66.

In this embodiment, the air conditioner 80 may include a housing 82 having therein a suction port 84, the first discharge port 86 that dries the floor of the bathroom, and the second discharge port 88 that dries the interiors of one or more of the modules provided in the cabinet, a fan 94 provided inside the housing 82 that generates an air flow from the suction port 84 to the first discharge port 86 or to the second discharge port 88, and a vane 90 to direct the air flow in the housing 82 through the first discharge port 86 or through the second discharge port 88. The air conditioner 80 may further include a heater 92 for heating the air flowing therein. The air conditioner 80 further includes an air-conditioning filter (or grill) 96 that filters air that is suctioned into the suction port 84 of the housing 82.

The vane 90 may selectively open and close the first discharge port 86 or the second discharge port 88. The vane 90 may be driven by a vane-driving motor (not shown). The first discharge port 86 or the second discharge port 88 may be opened and closed by the operation of the vane-driving motor. The first discharge port 86 or the second discharge port 88 may be selectively opened and closed by the operation of the vane 90. For example, when vane 90 is positioned such that the first discharge port 86 is open, the second discharge port 88 is closed or blocked by the vane 90. Similarly, when the vane 90 is moved to block or otherwise close the first discharge port 86, the vane 90 may be positioned such that the second discharge port 88 is opened.

In one example, the first module 70 may receive and store utensils used in the bathroom. The first module 70 may function to dry the utensils. For example, the first module 70 may dry utensils received therein using hot (e.g., heated) air discharged from the air conditioner 80.

The first module 70 may include a first module drawer 72 movably provided in the cabinet and having a space defined therein, a basket 73 detachably provided in the first module drawer 72, and a rack 74 provided in the basket 73 for holding utensils. The interior of the first module drawer 72 may be hollow, and a top of the first module drawer 72 may be open such that the basket can be inserted into the drawer 72. Consequently, the basket 73 may be inserted or removed through the open top of the drawer. The first module 70 may further include a first module suction member (or a first module inlet) 76 having therein a suction channel connected to the air conditioner 80 (e.g., to the second discharge port 88) and a first module discharge member (or first module outlet) 77 having a discharge port for discharging air from the first module 70.

Figure 3:
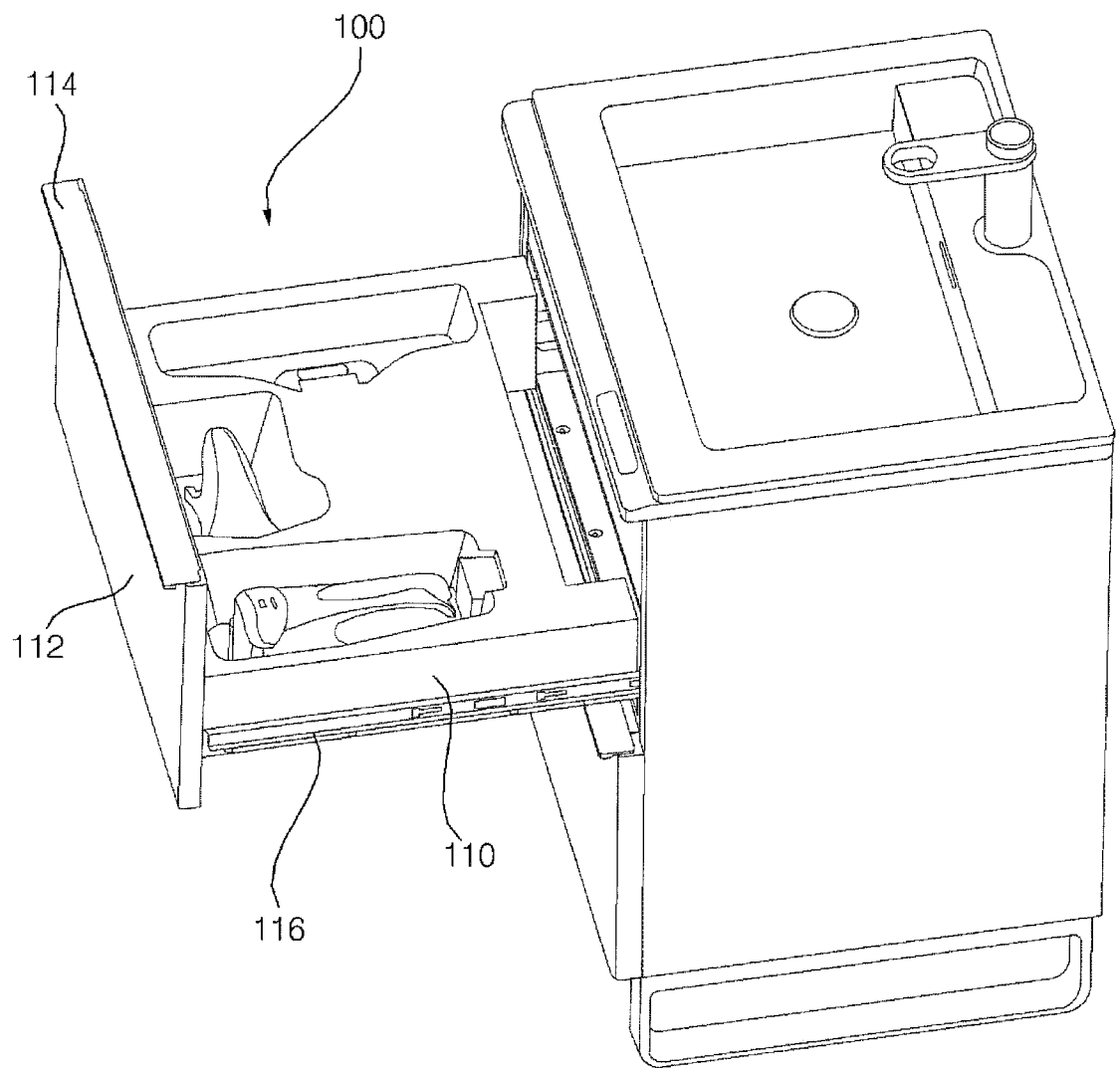
FIG. 3 is a view showing the state in which a second module of the washstand furniture according to the embodiment of the present disclosure is withdrawn.
Figure 4:
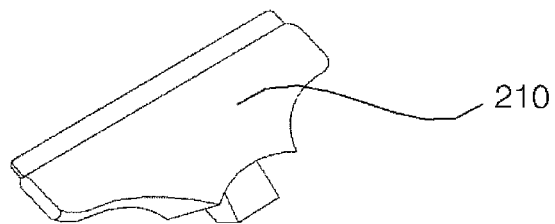
FIG. 4 is a view showing a residual water suction device received in a second module according to an embodiment of the present disclosure.
Figure 4:
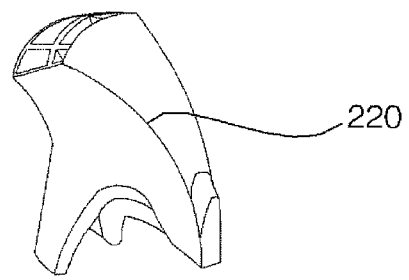
Figure 4:
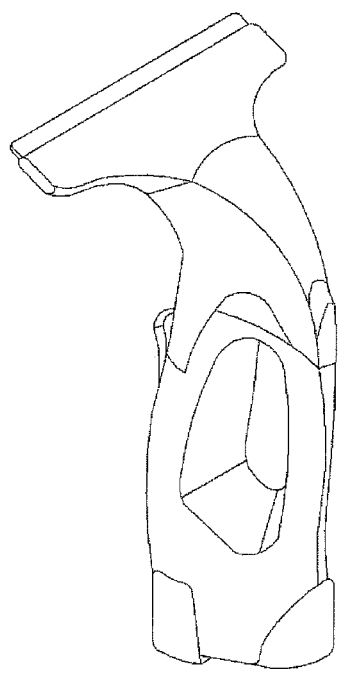
Figure 4:
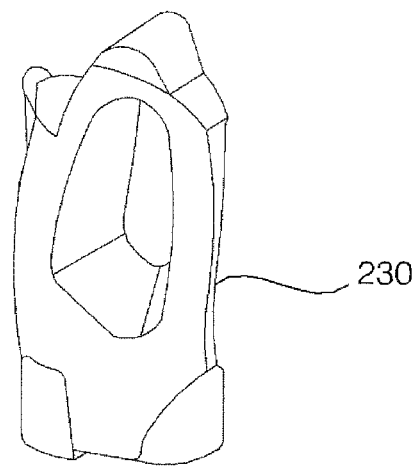
Figure 5:
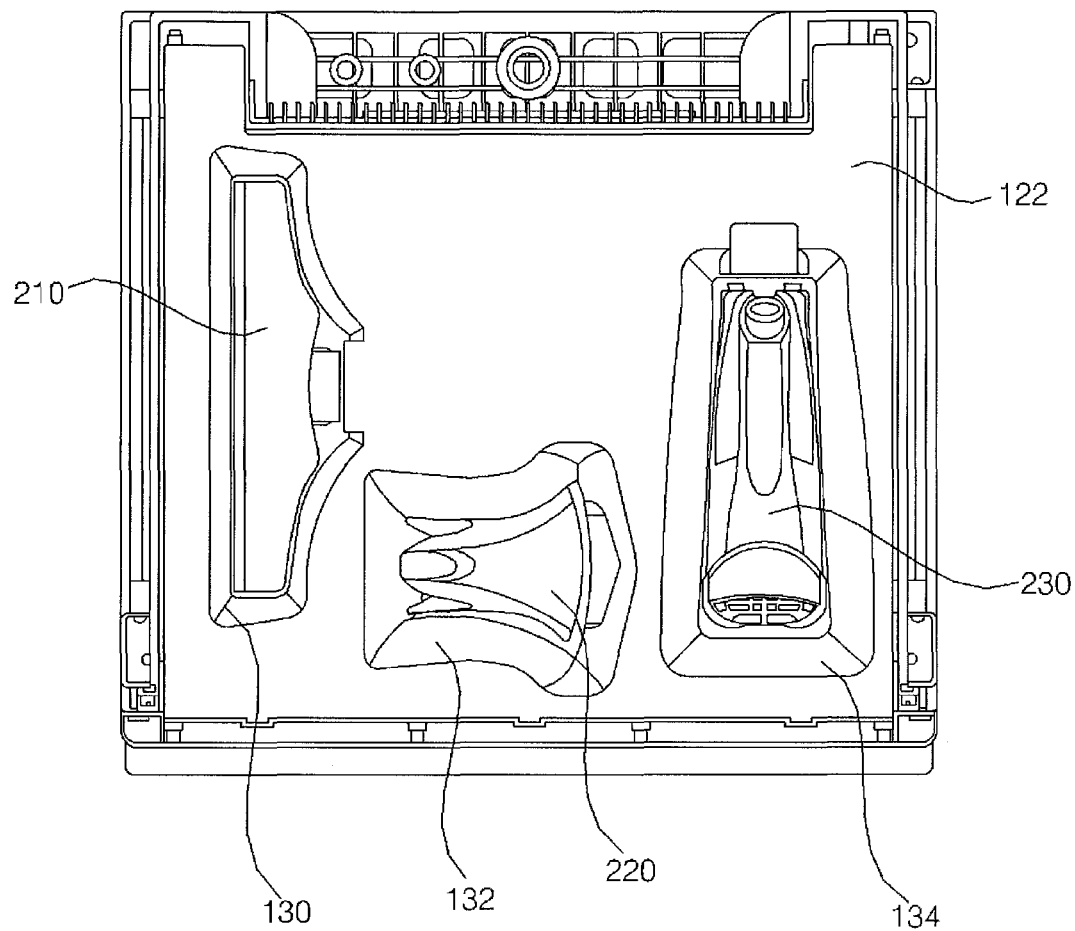
FIG. 5 is a sectional view taken along line V-V' of FIG. 1.
Figure 6:
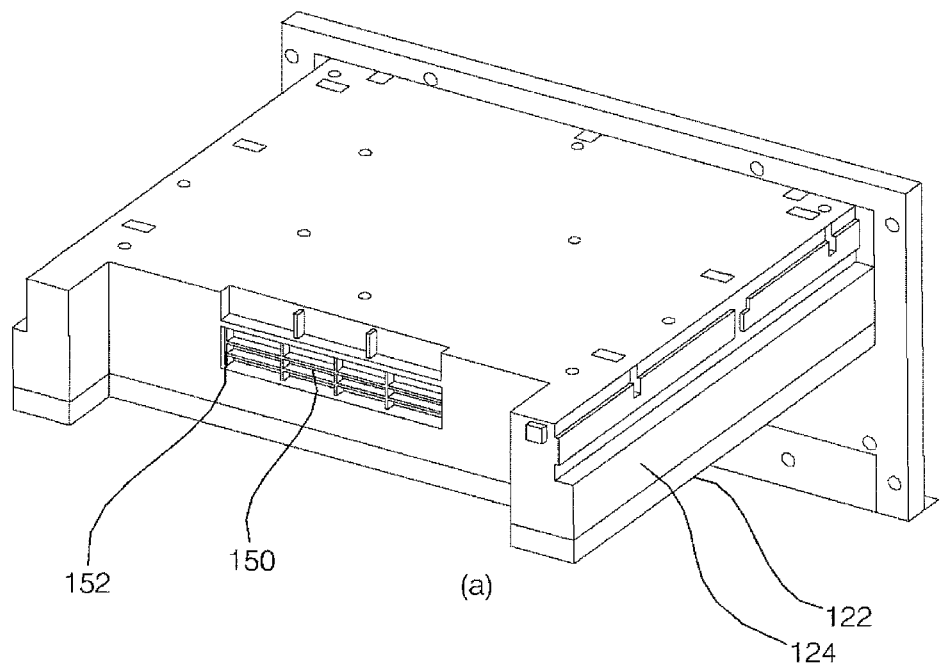
FIG. 6 shows a bottom perspective view of the second module, and a view of the second module when a lower cover is removed according to the embodiment of the present disclosure.
Figure 6:
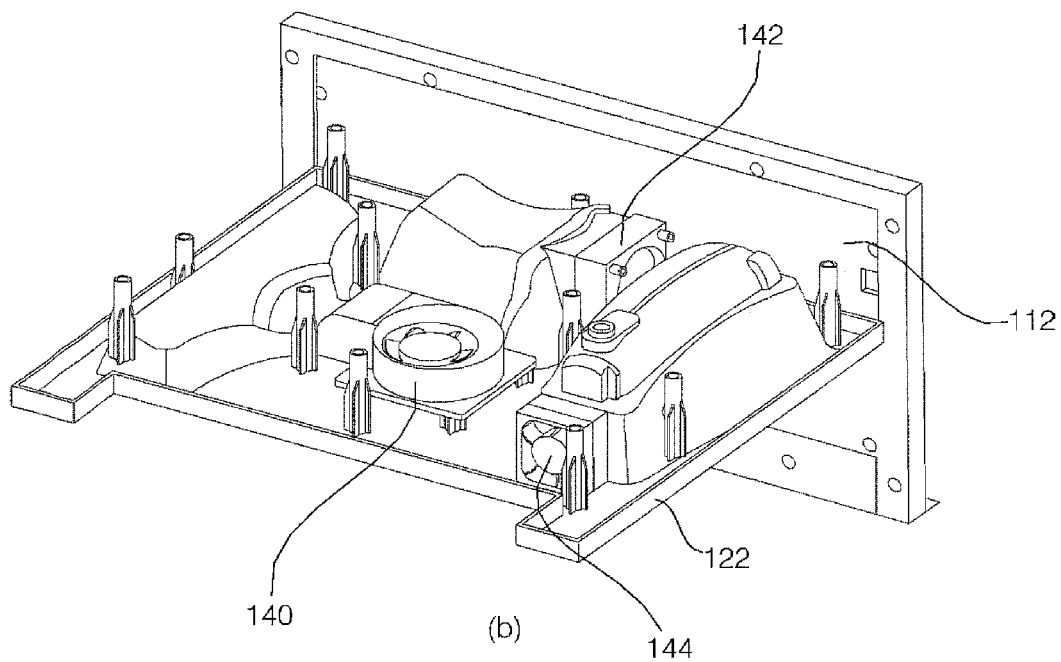
Figure 7:
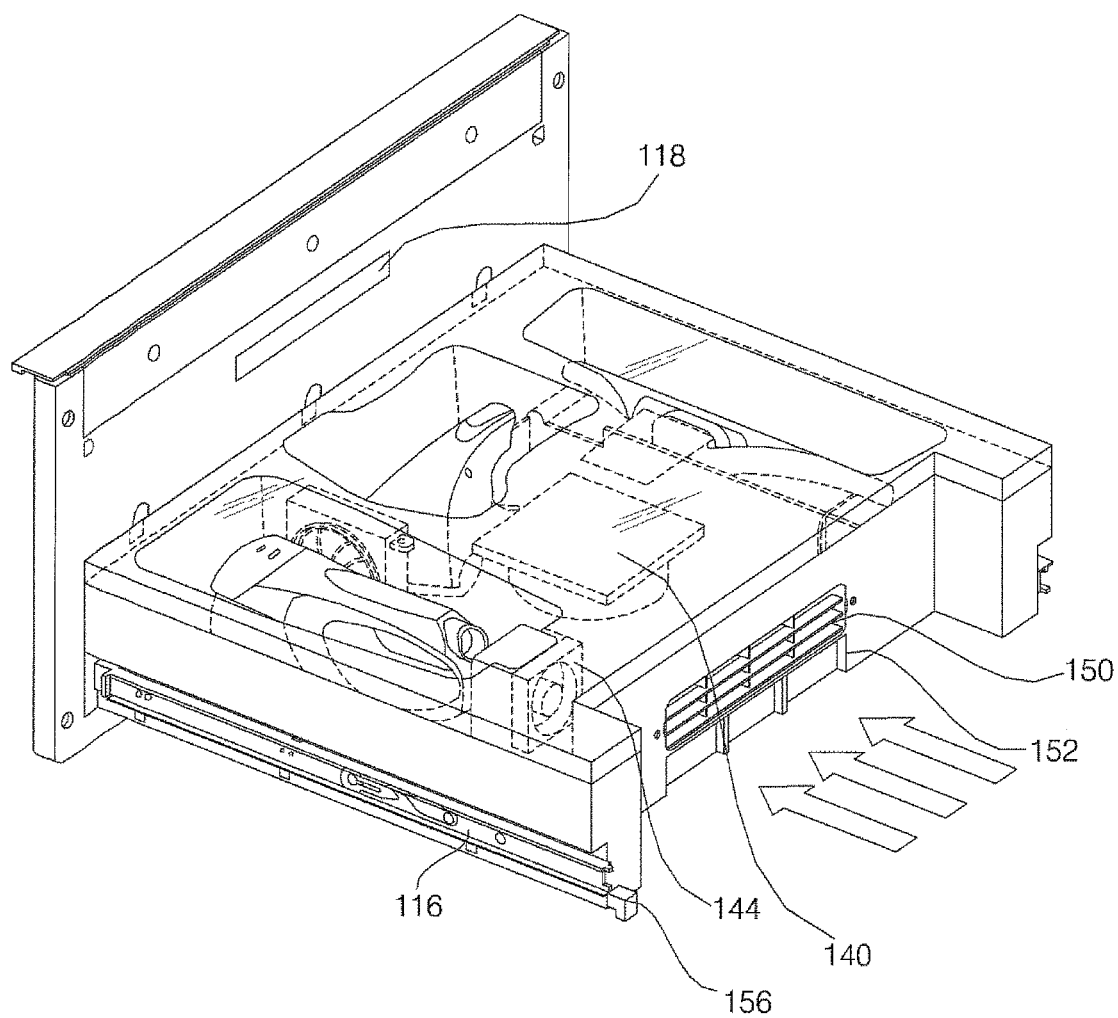
FIG. 7 is a view illustrating a plurality of fans provided between an upper cover and a lower cover according to an embodiment of the present disclosure.
Figure 8:
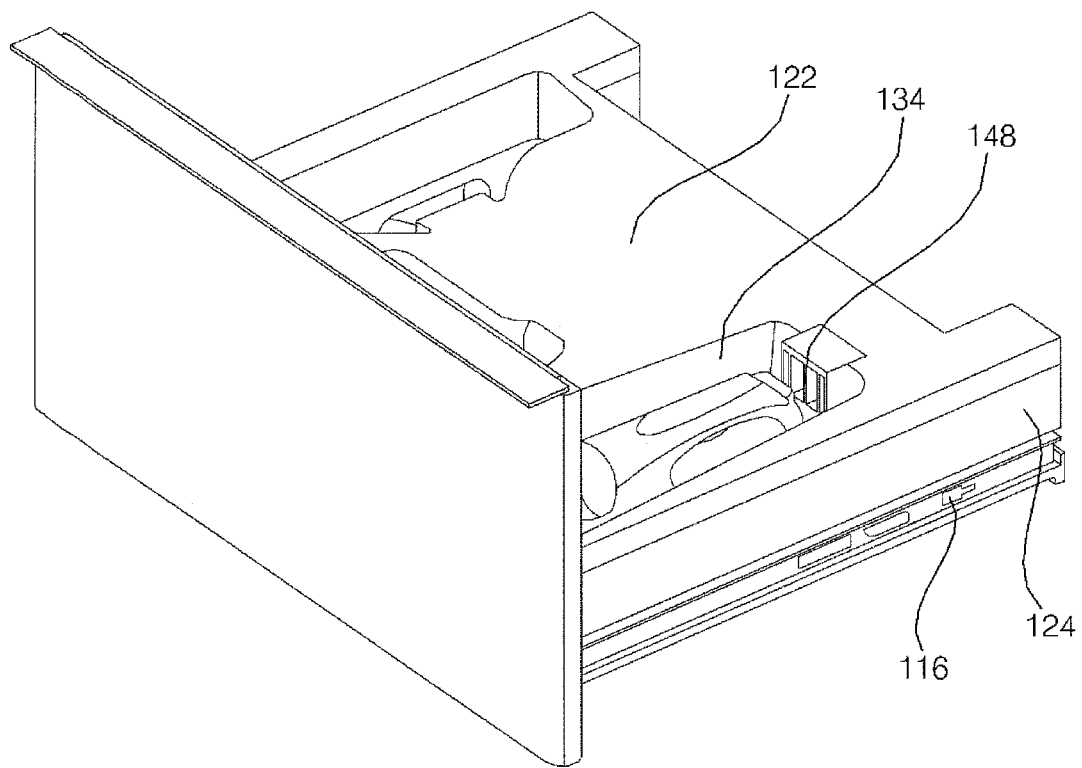
FIG. 8 is a front perspective view showing the second module according to the embodiment of the present disclosure.
Figure 9:
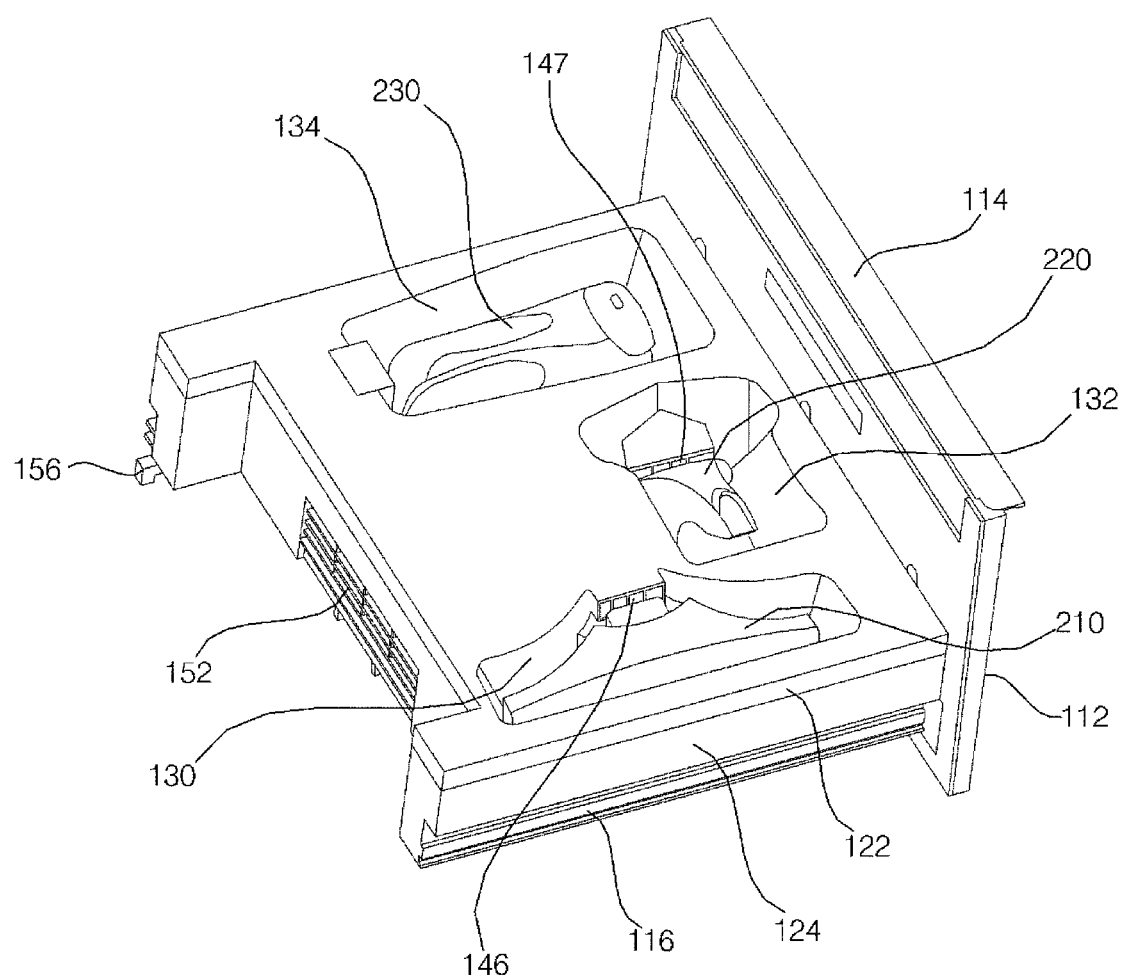
FIG. 9 is a rear perspective view showing the second module according to the embodiment of the present disclosure.
Figure 10:
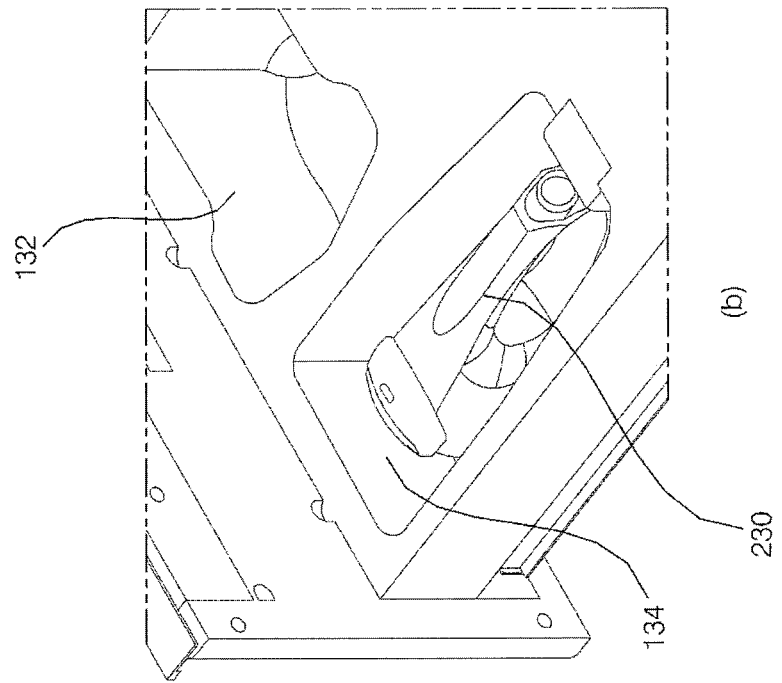
FIG. 10 shows a view showing a main body of a residual water suction device being inserted into a third reception unit in which a charging transmission unit is provided, and a view showing the main body of the residual water suction device after being received in the third reception unit where the charging transmission unit provided, according to an embodiment of the present disclosure.
Figure 10:
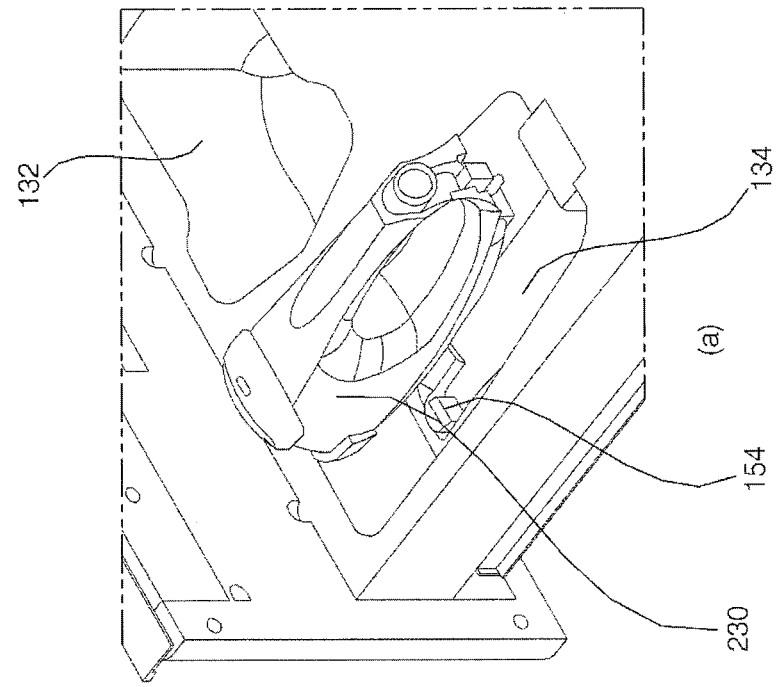

FIG. 3 is a view showing the state in which the second module 100 of the washstand furniture 10 according to the embodiment of the present disclosure is withdrawn, and FIG. 4 is a view showing a residual water suction device 200 received in the second module 100 according to the embodiment of the present disclosure. FIG. 5 is a sectional view taken along line V-V' of FIG. 1, and FIG. 6 is a view illustrating a lower cover 124 and an upper cover 122 of the second module 100 according to the embodiment of the present disclosure. FIG. 7 is a view illustrating a plurality of fans provided between the upper cover 122 and the lower cover 124 according to the embodiment of the present disclosure, and FIG. 8 is a front perspective view showing the second module 100 according to the embodiment of the present disclosure. FIG. 9 is a rear perspective view showing the second module 100 according to the embodiment of the present disclosure, and FIG. 10 is a view illustrating a charging transmission unit (or charger) 154 of the second module 100 according to the embodiment of the present disclosure. Hereinafter, the second module 100 will be described with reference to FIGS. 3 to 10.

In one embodiment, portions of a residual water suction device 200, which can be used in the bathroom to remove water, may be received in the second module (or the "residual-water-suction-device-drying module") 100. The second module 100 may dry or otherwise remove residual moisture from sections of the residual water suction device 200. Additionally, the second module 100 may perform other functions related to the residual water suction device 200, such as to charge a rechargeable battery in the residual water suction device 200.

The residual water suction device 200, which is received in the second module 100, will be described with reference to FIG. 4. The residual water suction device 200 may remove residual water from the wall, floors, or other surface of a bathroom by suctioning this water. In this embodiment, the residual water suction device 200 may include a main body 230 having a suction module for suctioning a fluid, a liquid-gas separator 220 connected to the main body 230 for separating the suctioned fluid into gas and liquid, and a suction nozzle 210 having a suction port for suctioning the fluid through the operation of the suction module. The main body 230 may include a drainage water tank connected to the liquid-gas separator 220 for storing the separated liquid. The main body 230 may further include a rechargeable battery for supplying electric power to the suction module of the residual water suction device 200 and an electric power reception unit for receiving external electric power.

In this embodiment, the residual water suction device 200 may be divided, for example, into the suction nozzle 210, the liquid-gas separator 220, and the main body 230. In other examples, the residual water suction device 200 may be separated into fewer, additional, or different components. The second module 100 may receive therein one or more of the suction nozzle 210, the liquid-gas separator 220, and the main body 230 of the residual water suction device 200 and may dry the received suction nozzle 210, liquid-gas separator 220, and/or main body 230.

The second module 100 may include a plurality of receiving spaces to accommodate the separate components of the residual water suction device 200. Referring to FIG. 5, the second module 100 may include a first reception unit (or first recess) 130 to accommodate the suction nozzle 210, a second reception unit (or second recess) 132 to accommodate the liquid-gas separator 220, and a third reception unit (or third recess) 134 to accommodate the main body 230. Although three separate reception units 130, 132, and 134 to receive three portions of the residual water suction device 200 are shown in the figures, it should be appreciated that the second module 100 may include additional, fewer, or different reception units.

The second module 100 may also include a first fan 140 to move air to the first reception unit 130, a second fan 142 to move air to the second reception unit 132, and a third fan 144 to move air to the third reception unit 134. Although three separate fans 140, 142, and 144 are shown in the figures, it should be appreciated that the second module 100 may include additional, fewer, or different fans.

The second module 100 may also include a drawer 110, which is movably provided in (e.g., to slide in or out of) the cabinet and which defines the plurality of reception units 130, 132, and 134 to accommodate the separate components of the residual water suction device 200, and the plurality of fans 140, 142, and 144 to move air to the respective reception units 130, 132, and 134. The second module 100 may include a front part (or front drawer wall) 112 provided at the front of the drawer 110 and a drawer handle 114 protruding from the upper end of the front part 112. The front part 112 may cover the open front of the cabinet.

A portion of the upper surface of the drawer 110 may be recessed inward to define the reception units 130, 132, and 134. The fans 140, 142, and 144 for moving air to the reception units 130, 132, and 134, respectively, may be provided in the drawer 110.

The drawer 110 may include, at the rear thereof, a suction member (or suction inlet) 152 having a suction port 150, through which air flows into the drawer 110. Referring to FIG. 7, the suction member 152 according to this embodiment may be separate from the drawer 110 and may be provided at one side of the drawer 110. Alternatively, the suction member 152 may be integrally formed with the drawer 110.

The second module 100 may include a moving rail 116 for inserting the drawer 110 into the cabinet or withdrawing the drawer 110 from the cabinet. In this embodiment, the moving rail 116 may be provided on the side surface of the drawer 110. A rail member may be provided inside the inner cabinet 40 at a position corresponding to the moving rail 116. As the moving rail 116 of the drawer 110 moves along the rail member of the inner cabinet 40, the drawer 110 may be inserted into or withdrawn from the inner cabinet 40.

The drawer 110 may include a wire connection member (or wire connection) 156 that connects an electric power supply wire to the interior of the drawer 110. The wire connection member 156 may be connected to the cabinet or the partition 50. The wire may be connected to the interior of the second module 100 through the wire connection member 156.

Referring to FIG. 7, the wire connection member 156 according to this embodiment may be provided at the rear surface of the drawer 110. The wire provided in the drawer 110 through the wire connection member 156 may supply electric power to various components in the first module 100, such as an ultraviolet lamp, which will be described in detail below, a charger, and/or to the fans 140, 142, 144.

Referring to FIG. 6, the drawer 110 may include an upper cover 122, which defines the upper surface of the drawer 110, and a lower cover 124, which defines the side surfaces, the rear surface, and the lower surface of the drawer 110. The upper cover 122 and the lower cover 124 may be coupled to each other to define an internal channel 126 (see FIG. 8) to receive air flowing via the external connection channel 68. The fans 140, 142, and 144 may be provided in the internal channel 126, which is defined by the coupling between the upper cover 122 and the lower cover 124.

As shown in the drawings, the suction member 152, which has the suction port 150 therein for allowing the external connection channel 68 and the internal channel 126 of the drawer 110 to communicate with each other therethrough, may be provided at one side of the lower cover 124. A portion of the upper cover 122 may be recessed downward to define the reception units 130, 132, and 134 for receiving the separate components of the residual water suction device 200. The upper cover 122 may include, therein, a plurality of holes 146, 147, and 148 through the air flowing passes between the respective fans and the reception units.

Referring to FIG. 9, the first reception unit 130 may have a first hole 146 that os formed in the direction in which the first fan 140 is provided. Referring to FIG. 9, the second reception unit 132 may have a second hole 147 formed in the direction in which the second fan 142 is provided. Referring to FIG. 8, the third reception unit 134 may have a third hole 148 that is formed in the direction in which the third fan 144 is provided.

The drawer 110 may include, at the rear thereof, a suction member (or suction inlet) 152 having a suction port 150, through which air flows into the drawer 110. As communication hole 48 may be formed in the inner cabinet 40 at a location corresponding to the suction port 150 of the drawer 110.

When the drawer 110 is inserted into the inner cabinet 40, the upper cover 122 of the drawer 110 may be positioned so as to be spaced apart from the upper surface 42 of the inner cabinet 40 by a predetermined distance. A discharge channel 160 may be defined between the upper cover 122 of the drawer 110 and the upper surface 42 of the inner cabinet 40, and the air discharged into the reception units by the fans may flow through the discharge channel 160. The communication hole 48, through which the air flowing in the discharge channel 160 is discharged to the external connection channel 68, may be formed in the upper end of the rear surface of the inner cabinet 40.

The drawer 110 may include a charging transmission unit (or charge transmission antenna) 154 that charges a rechargeable battery in the residual water suction device 200. Referring to FIG. 10, the charging transmission unit 154 may be provided at one side of the third reception unit 134, in which the main body 230 of the residual water suction device 200 is received.

The charging transmission unit 154 may supply electric power to a charging reception unit (or a charge reception antenna) in a wireless fashion. For example, the charging transmission unit 154 may generate induction voltage, and the charging reception unit receives the induction voltage, whereby electric power is supplied to the charging reception unit in a wireless fashion via the induction voltage. Since the residual water suction device 200 may be used in a humid space such as a bathroom, electric power may be supplied to the residual water suction device 200 in a wireless fashion. Alternatively, an electric docking station may be provided for charging the residual water suction device 200 through electric docking in which the residual water suction device 200 is connected to a power supply when received in the module 100. When the main body 230 is received in the third reception unit 134, therefore, the rechargeable battery in the main body 230 may be charged.

The second module 100 may further include an ultraviolet lamp 118 to sterilize one or more of the separated components of the residual water suction device 200. Since the components of the residual water suction device 200 are separated, the sterilizing light from the ultraviolet lamp 118 may reach an interior of the residual water suction device 200. In this embodiment, the ultraviolet lamp 118 may be provided inside the front part (or drawer front) 112. Alternatively, separate ultraviolet lamps may be provided in the respective reception units, in which the separate components of the residual water suction device 200 are positioned.

Figure 11:
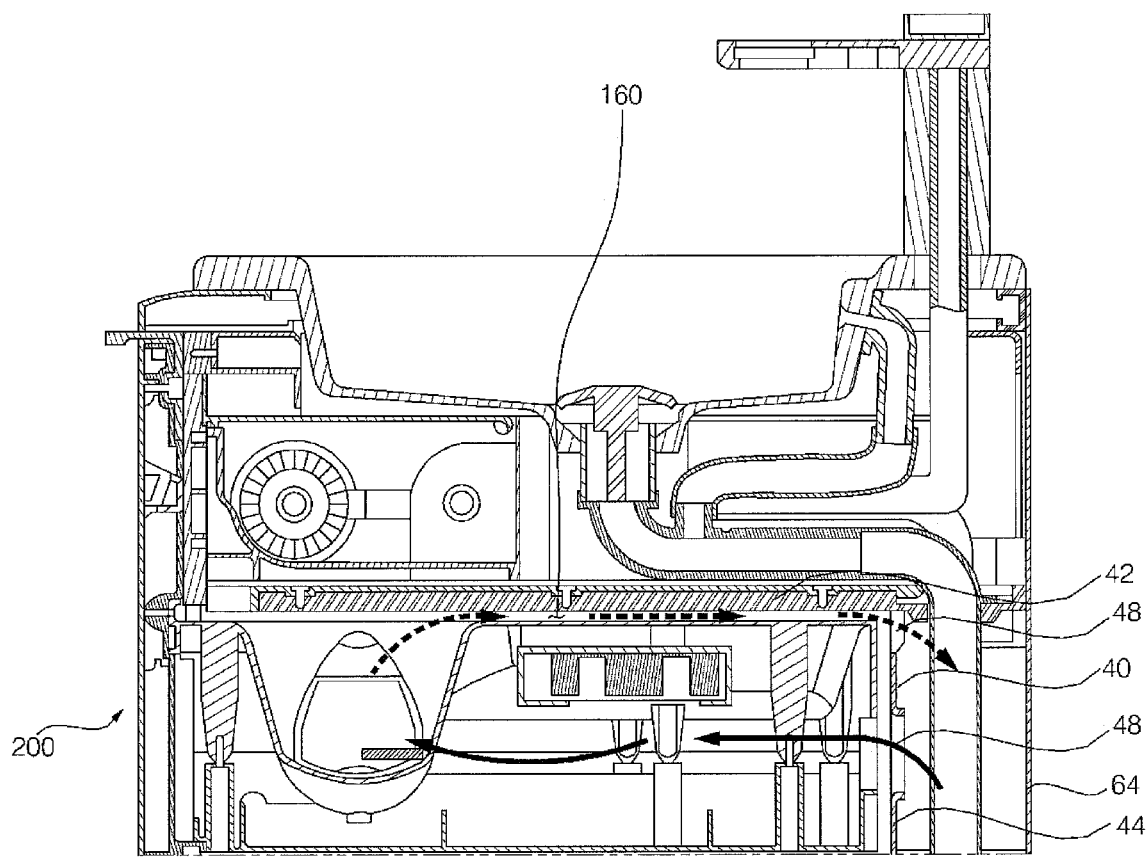
FIG. 11 is a view illustrating the flow of air in the second module according to the embodiment of the present disclosure.

FIG. 11 is a view illustrating the flow of air in the second module 100 according to the embodiment of the present disclosure. Hereinafter, the flow of air inside and outside the second module 100 due to the operation of the fans provided in the second module 100 will be described.

When the fans 140, 142, and 144 in the drawer 110 are operated, air may be introduced from the external connection channel 68 into a space 136 defined in the drawer 110. The air introduced into the drawer 110 may be discharged into the reception units due to the operation of the fans. The air discharged into the reception units may dry the separate components of the residual water suction device 200, flow along the space defined between the upper cover 122 of the drawer 110 and the upper surface 42 of the inner cabinet 40, and may be discharged to the external connection channel 68 through the communication hole 48 formed in the inner cabinet.

As is apparent from the above description, the washstand furniture according to the present disclosure has the following aspects. First, the washstand furniture includes a residual-water-suction-device-drying module that receives and dries separate components of a residual water suction device. Consequently, it is possible to effectively remove moisture from the residual water suction device while holding the residual water suction device. Second, the residual-water-suction-device-drying module may include a drawer having a plurality of reception units to receive the separate components of the residual water suction device and a plurality of fans for moving air to the respective reception units of the drawer. Consequently, the separate components of the residual water suction device are separately dried, whereby it is possible to thoroughly remove moisture from within the residual water suction device.

Third, the residual-water-suction-device-drying module may include a charging transmission unit to charge one or more components the residual water suction device. Consequently, it is possible to freely use the charging transmission unit while the residual water suction device is being held and stored so that the charging transmission unit is ready to be used.

It is an aspect of the present disclosure to provide washstand furniture that is capable of holding and drying a residual water suction device for removing moisture from the wall of a bathroom. It is another aspect of the present disclosure to provide washstand furniture that is capable of holding and charging a residual water suction device. The aspects of the present disclosure are not limited to the above-mentioned aspects, and other aspects that have not been mentioned above will become evident to those skilled in the art from the following description.

In accordance with the present disclosure, the above and other aspects can be accomplished by the provision of washstand furniture including: a wash device including a wash bowl, a water supply assembly for supplying water to the wash bowl, and a drainage assembly for draining the water supplied to the wash bowl; a cabinet provided under the wash bowl, the cabinet having a space defined therein; and a residual-water-suction-device-drying module provided inside the cabinet for receiving and drying separate components of a residual water suction device for suctioning liquid. Consequently, it is possible to separately hold the separate components of the residual water suction device in the space defined in the washstand furniture while drying the separate components of the residual water suction device.

The residual-water-suction-device-drying module may include a drawer movably provided in the cabinet for defining a plurality of reception units for receiving the separate components of the residual water suction device and a plurality of fans for moving air to the respective reception units. Consequently, it is possible to dry the separate components of the residual water suction device.

The drawer may include a suction member having therein a suction port, through which air flows into the drawer. A discharge channel, along which air discharged into the reception units by the fans flows, may be defined between the upper cover of the drawer and the upper surface of the inner cabinet. Consequently, air for drying the residual water suction device may flow to the inside and outside of the residual-water-suction-device-drying module.

The drawer of the residual-water-suction-device-drying module may include a charging transmission unit for charging the residual water suction device. Consequently, it is possible to charge the residual water suction device while drying the residual water suction device.

Those skilled in the art will appreciate that the present disclosure may be carried out in specific ways other than those set forth herein without departing from the spirit and essential characteristics of the present disclosure. The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. Washstand furniture comprising:
    a wash bowl;
    a faucet that supplies water to the wash bowl; and
    a drain to remove the water supplied to the wash bowl;
    a cabinet provided under the wash bowl, the cabinet having a space defined therein; and
    a drying module provided within the space defined in the cabinet, wherein:
        the drying module accommodates separate components of a residual water suction device to suction liquid and provides an air flow to dry to the separate components of the residual water suction device,
        the drying module includes:
            a drawer that is movably provided in the cabinet and defines a plurality of receiving spaces to accommodate the separate components of the residual water suction device; and
            a plurality of fans to generate the air flow to the respective receiving spaces, and
        the drawer includes:
            an upper cover that defines an upper surface of the drawer, a portion of the upper cover being recessed downward to define the receiving spaces that accommodate the separate components of the residual water suction device; and
            a lower cover provided under the upper cover, the lower cover being coupled to the upper cover to define one or more spaces in which the fans are accommodated.

2. The washstand furniture according to claim 1, wherein the upper cover includes a plurality of holes through which air moves between the fans and the receiving spaces.

3. The washstand furniture according to claim 1, wherein the drawer comprises a suction channel member having, therein, a suction port, through which air flows into the drawer from outside the dryer module.

4. The washstand furniture according to claim 1, wherein the cabinet includes:
    an inner cabinet configured to be open at a front thereof, the inner cabinet having the space defined therein; and
    a rear-outer cabinet provided outside a rear surface of the inner cabinet, and wherein
    an external connection channel, through which air flows from an interior of the drying module to an exterior of the drying module, is defined between a rear surface of the inner cabinet and the rear-outer cabinet.

5. The washstand furniture according to claim 1, wherein the cabinet includes:
    an inner cabinet having a space defined therein to receive the drying module; and
    an outer cabinet provided outside the inner cabinet for maintaining rigidity of the washstand furniture, and
    wherein the upper cover is positioned so as to be spaced apart from an upper surface of the inner cabinet by a predetermined distance.

6. The washstand furniture according to claim 5, wherein the outer cabinet includes:
    a side-outer cabinet walls that cover corresponding side surfaces of the inner cabinet;
    a rear-outer cabinet wall that covers a rear surface of the inner cabinet; and a base-outer cabinet wall that covers a lower surface of the inner cabinet.

7. The washstand furniture according to claim 5, wherein a discharge channel, along which air flows into the receiving spaces, is defined between the upper cover of the drawer and the upper surface of the inner cabinet.

8. The washstand furniture according to claim 7, wherein a communication hole, through which air flowing in the discharge channel is discharged to an outside of the inner cabinet, is formed in a rear surface of the inner cabinet.

9. The washstand furniture according to claim 1, wherein the drying module includes a charging transmitter to charge one or more components of the residual water suction device.

10. The washstand furniture according to claim 9, wherein the charging transmitter includes an electric docking station that contacts and charges one or more of the components of the residual water suction device accommodated in the drying module.

11. The washstand furniture according to claim 9, wherein the charging transmitter generates an induction voltage that charges one or more of the components of the residual water suction device accommodated in the drying module.

12. The washstand furniture according to claim 1, wherein the drying module includes an ultraviolet lamp that outputs radiation to sterilize one or more of the separate components of the residual water suction device accommodated in the dryer module.

13. The washstand furniture according to claim 1, further comprising a user interface, wherein the drying module is selectively activated based on an input received via the user interface.

14. The washstand furniture according to claim 1, wherein the cabinet is further configured to receive another module in the space, the other module being positioned under the drying module.

15. The washstand furniture according to claim 14, further comprising a dryer that includes a fan to generate an air flow and a heater to heat the air flow, the dryer providing the heated air flow to an interior of the other module.

16. The washstand furniture according to claim 15, wherein the dryer further includes a vane to selectively direct the heated air flow to the other module or to a floor surface under the washstand furniture.

17. Washstand furniture comprising:
a wash bowl;
a faucet that supplies water to the wash bowl; and
a drain to remove the water supplied to the wash bowl;
a cabinet provided under the wash bowl, the cabinet having a space defined therein; and
a drying module provided within the space defined in the cabinet, wherein:
the drying module accommodates separate components of a residual water suction device to suction liquid and provides an air flow to dry to the separate components of the residual water suction device,
the drying module includes:
a drawer that is movably provided in the cabinet and defines a plurality of receiving spaces to accommodate the separate components of the residual water suction device; and
a one or more fans to generate the air flow to the respective receiving spaces, and
the drawer includes a suction channel member having, therein, a suction port, through which air flows into the drawer from outside the dryer module.

18. The washstand furniture according to claim 17, wherein one or more regions on an upper surface of the drawer are recessed inward to define the receiving spaces.

19. The washstand furniture according to claim 17, wherein the cabinet includes:
an inner cabinet configured to be open at a front thereof, the inner cabinet having the space defined therein; and
a rear-outer cabinet provided outside a rear surface of the inner cabinet, and wherein
an external connection channel, through which air flows from an interior of the drying module to an exterior of the drying module, is defined between a rear surface of the inner cabinet and the rear-outer cabinet.

20. The washstand furniture according to claim 17, wherein the drying module includes an ultraviolet lamp that outputs radiation to sterilize one or more of the separate components of the residual water suction device accommodated in the dryer module.

* * * * *